United States Patent [19]

Winkler

[11] 4,384,578
[45] May 24, 1983

[54] BIO-MEDICAL FLOW SENSOR

[75] Inventor: H. Eugene Winkler, Friendswood, Tex.

[73] Assignee: The United States of America as represented by the Administrator of the National Aeronautics and Space Administration, Washington, D.C.

[21] Appl. No.: 254,688

[22] Filed: Apr. 16, 1981

[51] Int. Cl.³ .............................................. A61M 5/00
[52] U.S. Cl. ..................................... 604/114; 73/204; 128/DIG. 13; 604/151
[58] Field of Search ............ 128/214 R, 214 E, 214.2, 128/227, DIG. 13; 73/204; 222/54

[56] References Cited

U.S. PATENT DOCUMENTS

| | | | |
|---|---|---|---|
| 2,446,283 | 8/1948 | Hulsberg | 73/204 |
| 2,994,222 | 8/1961 | Laub | 73/204 |
| 3,091,239 | 5/1963 | Moeller | 128/214 F |
| 3,500,686 | 3/1970 | Bell | 73/204 |
| 3,990,443 | 11/1976 | Fletcher | 128/214 E |
| 4,029,094 | 6/1977 | Winicki | 128/214 E |

FOREIGN PATENT DOCUMENTS 604741 9/1978 Switzerland .................... 128/214 E

*Primary Examiner*—Dalton L. Truluck
*Attorney, Agent, or Firm*—Russell E. Schlorff; John R. Manning; Marvin F. Matthews

[57] ABSTRACT

A bio-medical flow sensor (FIG. 1) including a packageable unit of a bottle (10), tubing (11) and hypodermic needle (12) which can be pre-sterilized and is disposable. The tubing (11) has spaced apart tubular metal segments (18,19). The temperature of the metal segments and fluid flow therein is sensed by thermistors (23,24) and at a downstream location heat is input by a resistor 25 (FIG. 2) to the metal segment (19) by a control electronics (16, FIG. 2). The fluid flow and the electrical power required of the resistor (25) to maintain a constant temperature differential between the tubular metal segments (18,19) is a measurable function of fluid flow through the tubing (11). The differential temperature measurement is made in a control electronics 16 (FIG. 2) and also can be used to control a flow control valve or pump (17) on the tubing (11) to maintain a constant flow in the tubing (11) and to shut off the tubing when air is present in the tubing.

8 Claims, 2 Drawing Figures

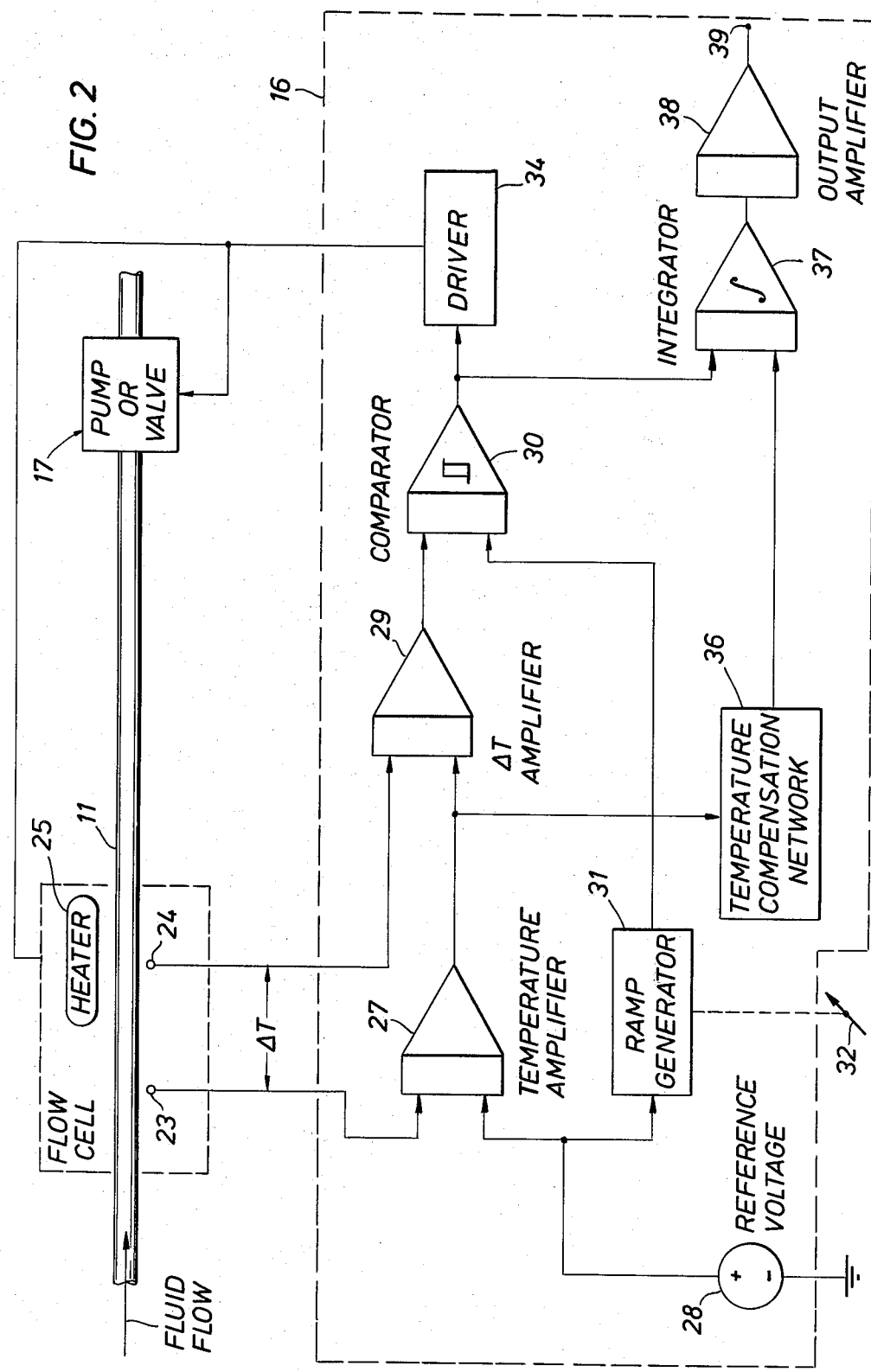

BIO-MEDICAL FLOW SENSOR

ORIGIN OF THE INVENTION

The invention described herein was made by an employee of the U.S. Government and may be manufactured and used by or for the Government of the United Stated of America for governmental purposes without the payment of any royalties thereon or therefor.

TECHNICAL FIELD

This invention relates to flow rate measuring and controlling devices, and more particularly, to a system for accurately measuring the flow rates of fluids introduced intravenously to medical patients and controlling of the flow rate of the fluids.

Currently, intravenous fluids such as whole blood, plasma or drugs in isotonic solutions are introduced through a needle coupled by a tubing to an elevated bottle of fluid. The elevated bottle of fluid provides a gravity fluid feed into a patient's vein. A small pinch valve is used to control the flow rate which is typically measured by timing the frequency of the drops at the mouth of the bottle. Generally, the entire intravenous system including the bottle, the tubing and a hypodermic needle are disposable which eliminates the need for sterilizing the equipment after each use.

The current methods of intravenous fluid injection have some disadvantages in that the flow rate varies widely as a function of the elevation of the bottle, the fluid level in the bottle and the temperature of the liquids. For some types of drug treatments, such as heparin therapy or chemotherapy, the rate of the drug injection is quite critical since excess doses can be toxic.

Peristaltic pumps are available which deliver fluid from a reservoir bottle through the tubing but significant disadvantages exist because if the fluid pressure varies upstream of the pump, the flow rate can change drastically if the tubing is not full to capacity. A drop counter method of flow measurement is extremely inaccurate since the size of the drops can vary widely and cause a plus or minus 15% error in the flow rate determination.

DISCLOSURE OF INVENTION

In accordance with the present invention I have provided a flow measuring system for accurately measuring the flow of intravenously injected fluids. The device includes two metal tubing segments in the delivery tube, a thermal flow sensor unit, control electronics and a proportioning valve or peristaltic pump. The thermal flow sensor unit uses thermistors for accurately measuring temperature at two points in the delivery tube. Specifically, the metal tubing segments are spaced a fixed distance apart from one another with a thermistor in thermal contact at each location. Before the fluid passes the downstream thermistor, a small resistor heats the downstream metal tubing segment sufficiently to keep the temperature sensed by the downstream thermistor at a predetermined level above that sensed by the upstream thermistor. The electric power consumed by the resistor to maintain the predetermined temperature differential between the locations is a measure of the flow rate. A flow control valve is regulated by the electrical sensing of temperature differential to increase or decrease the flow rate until the temperature differential is balanced to its pre-set condition. The advantages of the invention include its use as medical equipment.

BRIEF DESCRIPTION OF THE DRAWINGS

The details of my invention will best be described in connection with the accompanying drawing in which:

FIG. 2 is a schematic illustration of the electronics for the flow measuring system.

BEST MODE FOR CARRYING OUT THE INVENTION

Figure 1:
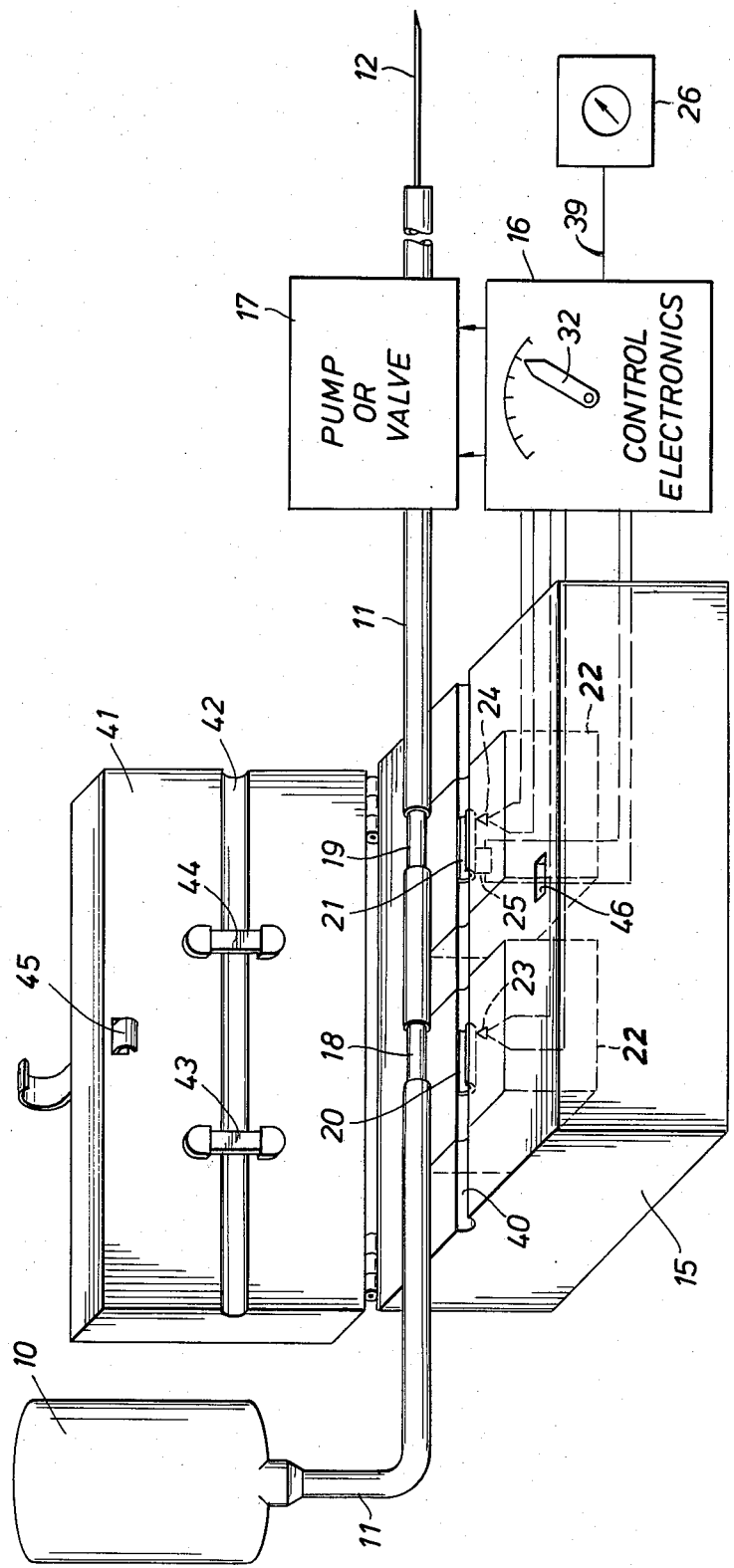
FIG. 1 is a perspective and schematic illustration of the flow measuring system.

Referring to the drawing, in FIG. 1 the system includes a supply bottle 10 of intravenous fluid, a plastic delivery tube 11 and an intravenous needle 12. Also included is a thermal flow sensor unit or container 15, control electronics 16, and flow control means 17.

The plastic delivery tube 11 has a pair of metal tubing segments 18 and 19 incorporated along its length at a fixed distance from one another. The metal tubing segments 18 and 19 are made of thin walled stainless steel or other highly thermal conductive metal such as silver or copper. The metal tubing segments 18 and 19 are arranged so as to be received in metal contact shells 20,21 disposed in a housing of the thermal flow sensor unit 15. The metal contact shells 20 and 21 are constructed of thermally conductive metal and curved to conform closely to the curvature of metal tubing segments 18 and 19 so that the tubing segments is snugly received by metal contact shells 20 and 21. Thermally conductive grease may be used to enhance the thermal connection between the metal tubing segments and the metal contact shells. Each of the metal contact shells is encased in an epoxy or plastic casting 22 to insulate the metal contact shells against loss of heat.

The upstream metal contact shell 20 is provided with a thermistor 23 for sensing temperature and for providing an electrical signal in response to sensed temperature. The downstream metal contact shell 21 is also provided with a thermistor 24 for sensing temperature and for providing an electrical signal in response to sensed temperature. On the upstream side of the metal contact shell 21, a resistor type heater 25 supplies heat to the metal contact shell. The power supplied to the resistor 25 is controlled so that the temperature of the tubing segment 19 is always a little higher than the temperature of tubing segment 18. As fluid flows through tubing segment 19, some of the heat is drawn away by the fluid and the temperature change is sensed by the thermistor 24. The control electronics 16, in response to the signal from thermistor 24 control the electrical power to the heater 25 to maintain a constant temperature difference between the two thermistors 23 and 24. The measurement of electrical power required to maintain this temperature difference provides an indication of fluid flow on a meter 26. Thus, the control electronics 16 constitutes a heat control means for controlling the heating means or heater 25 to regulate the amount of heat to the downstream metal tubing segment 19.

Between tubing segments 18 and 19 and the hypodermic needle 12, a proportioning valve 17 or a peristaltic pump may be incorporated, in the system, the valve 17 or pump being responsive to an electrical signal from the control electronics 16 to control the flow rate through the plastic tubing 11. Both the valve or pump 17 are well known and conventional in the art and need not be further described herein.

The control electronics 16 receives the electrical signals from thermistors 23 and 24 and measures the amount of current used by resistor 25 as an indication of flow rate of fluid in the tubing 11. If the flow rate in the tubing 11 varies from a predetermined flow rate, the control electronics 16 produces an electrical signal to the valve or pump 17 to adjust the flow rate to the predetermined flow rate.

Referring now to FIG. 2, where the control electronics 16 are illustrated in schematic form, the ambient temperature is sensed by the thermistor 23 and an electrical signal is supplied to the temperature amplifier 27 which also receives an input from a reference voltage source 28. The electrical signal from the second, downstream thermistor 24 is compared in a $\Delta T$ amplifier 29 with respect to the ambient temperature signal and supplies a comparison signal to a comparator circuit 30. The comparator circuit 30 also receives a signal from a ramp generator 31. The ramp generator 31 has a control means 32 which adjusts the ramp signal and thus, determines the pre-set temperature differential for the flow of fluid. The output of the comparator circuit 30 operates a driver circuit 34 which controls the electrical current in the heating resistor 25 as a function of the output of the comparator circuit. To obtain an indication of the flow rate on a meter 26, an electrical signal is supplied from the temperature amplifier 27 through a temperature compensation network 36 to an integrator circuit 37 which combines the electrical output of comparator 30 and the electrical output of representative of the ambient temperature to provide resultant electrical signal to an amplifier 38 and output terminal 39 where the output is proportional to the flow rate.

Referring again to FIG. 1, the thermal flow sensor unit 15 is illustrated as a box like container which contains a semi-cylindrical, lengthwise extending channel 40 for receiving the delivery tubing 11. Disposed within the sensor unit 15 along the surface of the channel 40 are the metal contact shells 20 and 21. The cover lid 41 of the sensor unit 15 has a corresponding semi-circular channel 42 with a spaced apart pressure plates 43 and 44 which are non-metallic and made of low thermal conductivity material. The plates 43 and 44 bear upon the metal tubing segments 18 and 19 when the cover lid 41 is closed to insure thermal contact of the segments 18 and 19 with the metal contact shells 20 and 21. To prevent heat loss, the channels 40 and 42 are sized to closely match the curvature of the tubing 11. A latch 45 in the cover lid 41 is received in a recess 46 in the bottom portion of the container for locking the cover lid 41 in a closed position. For good sensitivity and fast response time, the metal tubing segments 18 and 19 and the metal contact shells 20 and 21 should be made as small as is practical. Tests have shown the thermistor/heater technique of measuring fluid flow described herein can sense fluid flows as low as 100 drops per hour.

In operation of the system, the upstream thermistor 23 measures the ambient temperature of the incoming fluid. The resistance heater 25 supplies heat in the region around second downstream thermistor 24. The temperature of the downstream tubing segment 19 is always higher than the temperature of the upstream tubing segment 18 because of the heater 25. As the fluid flows by second thermistor 24, the temperature effect on the fluid is constant for a given flow rate as reflected by a temperature difference which is sensed by the second thermistor 24. The deviation of the temperature difference measurement relative to the temperature differential for a given flow rate is used to control the power applied to the heater 25 to maintain a constant temperature differential between thermistor 23 and thermistor 24 for a given flow rate.

In absence of fluid flow, the quantity of power required to maintain a constant change in temperature is equal to the amount of heat loss by conduction through the surrounding material to the outside. As flow beings and increases, a greater quantity of power is necessary to maintain the temperature difference. Since the ambient temperature of the fluid is measured by the upstream thermistor 23 and a constant temperature differential is maintained between the two thermistors 23 and 24, the flow sensor response is not affected by changes in the temperature of the solution.

This invention offers distinct advantages over the prior art. It is a much more accurate, precise method for measuring and controlling the flow rate of intravenous fluids. The flow can be set to a precise rate and the device will maintain that rate constant until the therapy is completed. Also, since the flow rate is continuously monitored, the pump or valve 17 can be controlled continuously to prevent variations in flow rate due to changes in upstream pressure. The flow rate can be adjusted on the described device to a much more exact value than with what is currently used. It has advantage over using just a peristaltic pump since it has the capability of shutting the pump off when the fluid reservoir is empty, eliminating the possibility of injecting air into the patient's veins. In this instance the control electronics 16 will develop a signal representation of a no flow condition when air replaces liquid in the delivery tube because of the temperature measurement. This electrical signal from the temperature measurement is applied to the pump or valve 17 to cause an immediate shutdown of the pump or valve. In addition, an audible signal can be used to alert medical personnel that the intravenous fluid is depleted. Since a peristaltic pump is a positive displacement device, the tubing connected to the pump will remain closed against force of the pump rollers, thereby preventing any siphoning action. The system would, therefore, remain in this safe configuration until medical personnel remove the intravenous apparatus or replace the empty reservoir.

The described invention is not affected by changes in fluid temperature because a temperature differential is being sensed. This is particularly important in the medical industry, since intravenous solutions, particularly whole blood, are often refrigerated and may not be completely at room temperature when being used.

The conventional intravenous equipment currently widely used in hospitals is completely disposable, including the reservoir bottle, the delivery tubing and the hypodermic needle. This eliminates the need for resterilization between uses. Ordinarily, the bottle, tubing and needle are sterilized; then the bottle is filled with the proper fluid. The complete unit is then packaged to prevent recontamination. The described invention likewise can be disposable. All that is necessary is to provide the two small metal tubing segments in the delivery tube, and the equipment can be sterilized and packaged exactly as is done with the conventional units. The flow sensing unit into which the delivery tube is encompassed is never in contact with the fluid in the system and therefore does not have to be sterilized.

I claim:

1. A flow sensing system for biomedical application in measurement of low flow rate intravenous fluids, the improvement including an intravenous fluid source, and intravenous injection unit and a delivery tubing interconnecting said fluid source and said intravenous injection unit;
   flow sensing means for sensing the rate of flow through the delivery tubing including spaced apart, thermally conductive tubing metal segments disposed in said delivery tubing;
   container means for enclosing said tubing metal segments, said enclosing means having thermal sensing means for providing a thermal connection with said metal tubing segments and for sensing the temperature at each of said metal tubing segments in said delivery tubing; said enclosing means having heating means for supplying heat at the downstream metal tubing segment;
   heat control means for controlling the heating means to regulate the amount of heat to said downstream metal segment as a function of the differential temperature between said two metal tubing segments; and
   further including flow control means for controlling the rate of fluid through said delivery tubing, said flow control means being located between said flow sensing means and said intravenous injection unit;
   said flow control means being coupled to said heat control means and responsive to said heat control means for controlling the flow of fluid through said delivery tubing.

2. The flow sensing system as claimed in claim 1 wherein said flow control means is a positive displacement pump.

3. The flow sensing system as claimed in claim 1 wherein said flow control means is a flow control valve.

4. The flow sensing system as claimed in claims 2 or 3 wherein said thermal sensing means for sensing the temperature is responsive to air in the delivery tubing for closing off said delivery tubing.

5. The flow sensing system as claimed in claim 1 wherein said intravenous fluid source, said delivery tubing and said intravenous injection unit are sterilizable and disposable as a unit.

6. The flow sensing system as defined in claim 1 wherein said container means has channel means which are adapted to releasably receive a section of delivery tubing containing said tubing metal segments, thermally conductive semi-circular shells disposed in said channel means for receiving said tubing metal segments, said thermal sensing means including thermistors for sensing the temperature of fluid in a tubing metal segment; said heating means including an electrical resistor element disposed forward of the location of a thermistor, said heat control means being responsive to electrical signals from said thermistors for regulating the electrical power used by said resistor element to maintain a constant temperature differential between said thermistors.

7. The flow sensing means as claimed in claim 6 wherein said container means has clamping plates for maintaining said tubing metal segments in contact with said semi-circular shells.

8. The flow sensing means as claimed in claim 1 and further including means responsive to said heat control means for visually indicating the flow rate through said delivery tubing.

* * * * *